(12) United States Patent
Daimo

(10) Patent No.: US 11,094,337 B2
(45) Date of Patent: Aug. 17, 2021

(54) COUGH DETECTION DEVICE, COUGH DETECTION METHOD, AND RECORDING MEDIUM

(71) Applicant: Panasonic Intellectual Property Corporation of America, Torrance, CA (US)

(72) Inventor: Katsunori Daimo, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 0 days.

(21) Appl. No.: 16/909,189

(22) Filed: Jun. 23, 2020

(65) Prior Publication Data
US 2020/0411036 A1 Dec. 31, 2020

(30) Foreign Application Priority Data

Jun. 25, 2019 (JP) .............................. JP2019-117220

(51) Int. Cl.
| | |
|---|---|
| *G10L 25/51* | (2013.01) |
| *H04R 1/40* | (2006.01) |
| *H04R 3/00* | (2006.01) |
| *G06N 5/04* | (2006.01) |
| *G06K 9/00* | (2006.01) |
| *G06N 20/00* | (2019.01) |

(52) U.S. Cl.
CPC .......... *G10L 25/51* (2013.01); *G06K 9/00335* (2013.01); *G06K 9/00624* (2013.01); *G06N 5/04* (2013.01); *G06N 20/00* (2019.01); *H04R 1/406* (2013.01); *H04R 3/005* (2013.01)

(58) Field of Classification Search
CPC ....... A61B 5/0823; A61B 5/11; A61B 5/7282; A61B 2562/0204; A61B 2576/00; A61B 5/1128; A61B 5/7405; A61B 5/721; A61B 2562/06; G10L 25/66; G10L 25/51; G10L 15/02; G10L 2021/02166; G06N 20/00; G06N 5/04; G06K 9/00335; G06K 9/00624; H04R 1/406; H04R 3/005
USPC ............. 381/56, 107, 67; 704/246, E15.004, 704/E17.002, 208
See application file for complete search history.

(56) References Cited

U.S. PATENT DOCUMENTS

| | | | |
|---|---|---|---|
| 2009/0312660 A1* | 12/2009 | Guarino | A61B 7/003 600/529 |
| 2018/0206764 A1* | 7/2018 | Ozawa | A61B 7/003 |

FOREIGN PATENT DOCUMENTS

| | | |
|---|---|---|
| JP | 2011-174624 | 9/2011 |
| JP | 2018-117708 | 8/2018 |

\* cited by examiner

*Primary Examiner* — Norman Yu
(74) *Attorney, Agent, or Firm* — Wenderoth, Lind & Ponack, L.L.P.

(57) ABSTRACT

A cough detection device including: an acoustic feature extractor that extracts at least one acoustic feature from acoustic data output by a microphone array according to a sound received; a first identifier that performs identification of the sound based on the at least one acoustic feature to determine whether the sound is a cough sound; a direction estimator that estimates an arrival direction of the sound from the acoustic data; an image selector that selects, from first image data indicating an image obtained by capturing a scene in which the sound occurs, second image data indicating an area corresponding to the arrival direction estimated; and a second identifier that performs identification of the image based on the second image data to determine whether a coughing action is shown in the image.

11 Claims, 9 Drawing Sheets

COUGH DETECTION DEVICE, COUGH DETECTION METHOD, AND RECORDING MEDIUM

CROSS REFERENCE TO RELATED APPLICATION

The present application is based on and claims priority of Japanese Patent Application No. 2019-117220 filed on Jun. 25, 2019. The entire disclosure of the above-identified application, including the specification, drawings and claims is incorporated herein by reference in its entirety.

FIELD

One or more exemplary embodiments disclosed herein relate generally to a cough detection technique of determining the occurrence of coughs.

BACKGROUND

A device that detects coughs using a sensor that is not worn on the body of a user has been proposed (see PTL 1). This device detects coughs based on motion information and audio information transmitted from a motion detector and an audio detector, respectively, which are provided for a seat where a person is seated.

CITATION LIST

Patent Literature

PTL 1: Japanese Unexamined Patent Application Publication No. 2018-117708

SUMMARY

Technical Problem

In the detection of coughs using the above-mentioned device, however, noise in a place where the device is used, such as a crashing sound or friction noise between objects, is erroneously detected as a cough sound due to the nature of cough sound which has many voiceless sound components.

One non-limiting and exemplary embodiment provides a cough detection device, a cough detection method, and a non-transitory computer-readable recording medium having a computer program for cough detection recorded thereon which are capable of detecting coughs with higher accuracy.

Solution to Problem

In one general aspect, the techniques disclosed here feature a cough detection device including: an acoustic feature extractor that extracts at least one acoustic feature from acoustic data that is output by a microphone array according to a sound received as an input; a first identifier that performs identification of the sound based on at least one acoustic feature extracted, to determine whether the sound is a cough sound; a direction estimator that estimates an arrival direction of the sound from the acoustic data; an image selector that selects, from first image data indicating an image obtained by capturing a scene in which the sound occurs, second image data indicating an area corresponding to the arrival direction estimated; a second identifier that performs identification of the image based on the second image data to determine whether a coughing action is shown in the image; and an output unit that performs output based on at least one of a determination result from the first identifier or a determination result from the second identifier.

In one general aspect, the techniques disclosed here feature a cough detection method including: extracting at least one acoustic feature from acoustic data that is output by a microphone array according to a sound received as an input; performing identification of the sound based on at least one acoustic feature extracted, to determine whether the sound is a cough sound; estimating an arrival direction of the sound from the acoustic data; selecting, from first image data indicating an image obtained by capturing a scene in which the sound occurs, second image data indicating an area corresponding to the arrival direction estimated; performing identification of the image based on the second image data to determine whether a coughing action is shown in the image; and determining occurrence of coughs based on at least one of a determination result indicating whether the sound is a cough sound or a determination result indicating whether a coughing action is shown in the image.

In one general aspect, the techniques disclosed here feature a non-transitory computer-readable recording medium, for use in a computer, having a computer program recorded thereon for causing the computer to execute: extracting at least one acoustic feature from acoustic data that is output by a microphone array according to a sound received as an input; performing identification of the sound based on at least one acoustic feature extracted, to determine whether the sound is a cough sound; estimating an arrival direction of the sound from the acoustic data; selecting, from first image data indicating an image obtained by capturing a scene in which the sound occurs, second image data indicating an area corresponding to the arrival direction estimated; performing identification of the image based on the second image data to determine whether a coughing action is shown in the image; and determining occurrence of coughs based on at least one of a determination result indicating whether the sound is a cough sound or a determination result indicating whether a coughing action is shown in the image.

General and specific aspect(s) disclosed above may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

The cough detection device, cough detection method, and non-transitory computer-readable recording medium having a computer program recorded thereon according to one or more exemplary embodiments or features disclosed herein provide cough detection with higher accuracy.

DESCRIPTION OF DRAWINGS

These and other advantages and features will become apparent from the following description thereof taken in conjunction with the accompanying Drawings, by way of non-limiting examples of embodiments disclosed herein.

Figure 1:
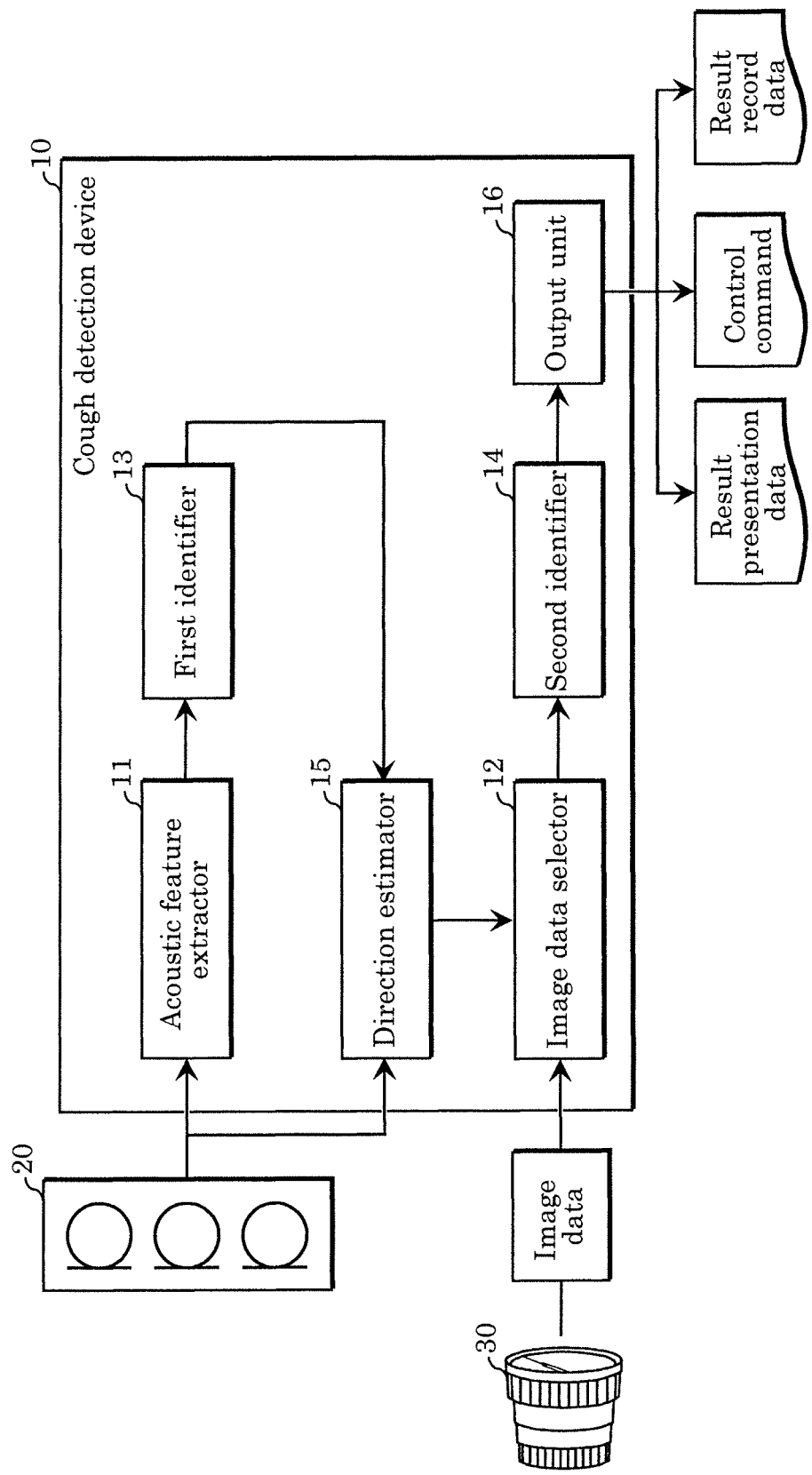
FIG. 1 is a block diagram illustrating an example of a configuration of a cough detection device according to an embodiment.

DESCRIPTION OF EMBODIMENT (Underlying Knowledge Forming Basis of the Present Disclosure)

The following is performed as a conventional method to detect coughs: extracting acoustic features from acoustic data obtained from a microphone; and determining whether a sound received by the microphone is a cough sound based on the acoustic features extracted, using an identifier. For example, mel-frequency cepstrum coefficients (MFCC) are used for acoustic features. The identifier performs, for example, identification based on a similarity between the acoustic features and a Gaussian mixture model (GMM) acoustic model or identification based on a deep neural network (DNN) inference model that uses acoustic features as an input.

However, being a voiceless sound, a cough sound does not have a cyclical spectral structure. Therefore, the problem with the identification using a cough sound data model as described above is that noise that occurs in the vicinity of the device is easily misidentified as a cough sound.

A multi-modal cough detection method using sensor data other than acoustic data is one example of a solution to such a problem. The sensor data other than acoustic data is, for example, data that may indicate a human motion sensed in a sensing area of an infrared sensor, for instance. When the occurrence of sounds sounding like coughs synchronizes with the occurrence of a predetermined human motion, the identifier determines that coughs have occurred.

With this method, however, there is a risk that, for example, a human motion occurred in a sensing area without any relation to the occurrence of sounds sounding like coughs is used for the determination. In other words, a false detection may occur when sounds sounding like coughs and a motion having no relation with coughing occur at the same time in the sensing areas of a sound sensor and an infrared sensor.

After a single-minded dedication to overcome the aforementioned problem, the inventor has arrived at a cough detection device, a cough detection method, and a non-transitory computer-readable recording medium having a computer program for cough detection recorded thereon which are capable of reducing the risk of such false detection, which will be described below.

According to an exemplary embodiment disclosed herein, a cough detection device includes: an acoustic feature extractor that extracts at least one acoustic feature from acoustic data that is output by a microphone array according to a sound received as an input; a first identifier that performs identification of the sound based on at least one acoustic feature extracted, to determine whether the sound is a cough sound; a direction estimator that estimates an arrival direction of the sound from the acoustic data; an image selector that selects, from first image data indicating an image obtained by capturing a scene in which the sound occurs, second image data indicating an area corresponding to the arrival direction estimated; a second identifier that performs identification of the image based on the second image data to determine whether a coughing action is shown in the image; and an output unit that performs output based on at least one of a determination result from the first identifier or a determination result from the second identifier.

With this, among a sound identified based on at least one acoustic feature, an estimated arrival direction of the sound, and image data, whether coughing has occurred is determined based on image data indicating an area in a range corresponding to the estimated arrival direction of the sound. Accordingly, when a seemingly coughing action simultaneously occurs with sounds sounding like coughs in a location that is not in the range corresponding to the arrival direction of the sound, it is possible to reduce the risk of determining that a human action of coughing is shown in an image.

The direction estimator may estimate the arrival direction of the sound determined as a cough sound by the first identifier. Moreover, the first identifier may determine whether the sound is a cough sound based on at least one acoustic feature extracted of the acoustic data temporally corresponding to the image determined as showing a coughing action by the second identifier.

In this way, either of the following may be performed first: the identification based on whether a sound is a cough sound; and the identification based on whether a coughing action is shown in an image indicating an area corresponding to the arrival direction of a sound.

For example, the second identifier may perform the identification of the image based also on an other portion other than the second image data in the first image data to determine whether a coughing action is shown in the image, and in the identification, priority may be given to the second image data over the other portion.

In this way, it is possible to reduce the risk of determining that coughs have occurred when an action similar to a coughing action occurs in an area corresponding to the arrival direction of a sound within the shooting range of an image sensor.

For example, the first identifier may be a first inference model obtained through machine learning, and the output unit may output retraining data for the first inference model when the determination result from the first identifier is different from the determination result from the second identifier regarding the occurrence of coughs. Moreover, the output unit may further output the retraining data for the first inference model when likelihood of the determination by the second identifier is higher than likelihood of the determination by the first identifier.

In this way, accuracy in sound identification based on acoustic features can be enhanced.

For example, the second identifier may be a second inference model obtained through machine learning, and the output unit may output retraining data for the second inference model when the determination result from the first identifier is different from the determination result from the second identifier regarding the occurrence of coughs. Moreover, the output unit may further output the retraining data for the second inference model when likelihood of the determination by the first identifier is higher than likelihood of the determination by the second identifier.

In this way, accuracy in image identification can be enhanced.

For example, the image may comprise a plurality of images obtained by a plurality of image sensors capturing at least partly different areas of the scene, and each of the plurality of image sensors may output, as the first image, image data of a corresponding one of the plurality of images. The image selector may (i) select, from among the plurality of image sensors, an image sensor provided in a location corresponding to the arrival direction estimated and (ii) cause the first image data output from the image selector to be input, as the second image data, to the second identifier.

Thus, the image data may include data that is output from a plurality of image sensors, and the identification of a coughing action may be performed based on image data output from one or more of the plurality of image sensors.

For example, the microphone array may comprise a plurality of microphone arrays. The direction estimator may estimate an occurrence location of the sound using the arrival direction estimated from a plurality of acoustic data items that are output by the plurality of microphone arrays. The second image data selected by the image selector may indicate the area corresponding to the occurrence location estimated.

By thus estimating the occurrence location of a sound, it is possible to more efficiently respond to coughs with higher locality, for example, by operating a device that produces antibacterial effects.

For example, a cough detection method according to one aspect of the present disclosure includes: extracting at least one acoustic feature from acoustic data that is output by a microphone array according to a sound received as an input; performing identification of the sound based on at least one acoustic feature extracted, to determine whether the sound is a cough sound; estimating an arrival direction of the sound from the acoustic data; selecting, from first image data indicating an image obtained by capturing a scene in which the sound occurs, second image data indicating an area corresponding to the arrival direction estimated; performing identification of the image based on the second image data to determine whether a coughing action is shown in the image; and determining occurrence of coughs based on at least one of a determination result indicating whether the sound is a cough sound or a determination result indicating whether a coughing action is shown in the image.

For example, a non-transitory computer-readable recording medium, for use in an information processing device including a processor and a memory, has a computer program recorded thereon for causing the information processing device to execute the following by the processor executing the computer program stored in the memory: extracting at least one acoustic feature from acoustic data that is output by a microphone array according to a sound received as an input; performing identification of the sound based on at least one acoustic feature extracted, to determine whether the sound is a cough sound; estimating an arrival direction of the sound from the acoustic data; selecting, from first image data indicating an image obtained by capturing a scene in which the sound occurs, second image data indicating an area corresponding to the arrival direction estimated; performing identification of the image based on the second image data to determine whether a coughing action is shown in the image; and determining occurrence of coughs based on at least one of a determination result indicating whether the sound is a cough sound or a determination result indicating whether a coughing action is shown in the image.

Even with such a method or recording medium, among a sound identified based on at least one acoustic feature, an estimated arrival direction of the sound, and image data, whether coughing has occurred is determined based on image data indicating an area in a range corresponding to the estimated arrival direction of the sound. Accordingly, when a seemingly coughing action simultaneously occurs with sounds sounding like coughs in a location that is not in the range corresponding to the arrival direction of the sound, it is possible to reduce the risk of determining that a human action of coughing is shown in an image.

Although the present disclosure describes that coughs are targeted for detection, the cough detection device, cough detection method and recording medium according to the present disclosure can be used also for the detection of sneezing. Coughs and sneezing are different in terms of occurrence mechanism, but both of them are actions to forcibly exhaust air through breathing passages to remove foreign substances therefrom to outside the body. In addition, coughs and sneezing each come out with a fast and big motion and a big sound compared with normal breathing, and the sound may include a high percentage of non-cyclic frequency components compared with sounds emitted in utterances. The air exhausted out of the body by coughing or sneezing includes foreign substances that were in breathing passages and mainly includes secretions such as saliva in droplets. The result of detection of coughs or sneezing occurrence performed, with high accuracy, by the cough detection device and so on according to the present disclosure can be used for, for example, the observation of health conditions or the maintenance of air quality (e.g., purification of air by an air cleaner or air infiltration by a ventilator). In view of this, the term "coughs" used herein as a target for detection performed by the cough detection device according to the present disclosure can also mean "sneezing". Moreover, "cough sound" may also mean "sneezing sound" and "coughing action" may also mean "sneezing action". It is to be understood that coughs and sneezing may be differentiated in the detection process and detection results thereof, but such differentiation is not essential.

Note that these comprehensive or concrete embodiments may be realized by a system, a method, an integrated circuit, a computer program, or a computer-readable recording medium such as a CD-ROM, or any combination of systems, methods, integrated circuits, computer programs, or computer-readable recording media.

Hereinafter, certain exemplary embodiments are described in greater detail with reference to the accompanying Drawings.

The following describes concrete examples of the cough detection device, the cough detection method, etc. according to one or more aspects of the present disclosure with reference to the drawings. The embodiment described herein shows a general or specific example of the present disclosure. Accordingly, the numerical values, shapes, elements, the arrangement and connection of the elements, steps (processes), the processing order of the steps, etc. shown in the following exemplary embodiment are mere examples, and therefore do not limit the scope of the appended Claims and their equivalents. Among the elements in the following exemplary embodiment, those not recited in any one of the independent claims presenting the embodiment according to one aspect of the present disclosure are described as optional elements. The embodiment of the present disclosure should not be limited to independent claims currently presented and may be also expressed by way of other independent claims. The drawings are presented schematically for explaining the concepts according to the present disclosure, and shapes, quantities, arrangements, scales, and size relationships are not necessarily precise illustrations.

EMBODIMENT

[1. Configuration of Cough Detection Device]

Cough detection device 10 according to an embodiment determines whether a person coughs (cough detection) in a space in a room which people use or frequently visit. In addition, cough detection device 10 outputs, for instance, data indicating the result of the determination.

FIG. 1 is a block diagram illustrating an example of a configuration of cough detection device 10. Cough detection device 10 that functions as described above includes acoustic feature extractor 11, image data selector 12, first identifier 13, second identifier 14, direction estimator 15, and output unit 16. Cough detection device 10 is realized using, for example, an information processing device including a processor and a memory, and the elements included in cough detection device 10 are functional elements realized by the processor executing one or more programs stored in the memory.

Microphone array 20 and camera 30 are connected to cough detection device 10. In cough detection device 10, acoustic feature extractor 11 and direction estimator 15 receive an input of acoustic data that is output by microphone array 20 according to a sound received. Acoustic feature extractor 11 extracts acoustic features from the acoustic data received. The acoustic features are, for example, MFCC. Direction estimator 15 estimates the arrival direction of the sound received by microphone array 20. The arrival direction of the sound is estimated based on a time difference between the inputs of the sound to microphone elements included in microphone array 20. Image data output by camera 30 is input to image data selector 12. An image capturing element that is included in camera 30 and generates the image data is, for example, an image sensor that outputs, as image data, visible or infrared light that has been sensed.

First identifier 13 performs identification of a sound received by microphone array 20 based on the acoustic features extracted by acoustic feature extractor 11, to determine whether the sound is a cough sound. The identification is carried out using, for example, a statistic acoustic model of cough sound which is previously prepared based on feature data of sound extracted from a massive amount of acoustic data recording cough sounds. In this case, when a similarity between the acoustic features extracted by acoustic feature extractor 11 and this acoustic model exceeds a threshold value, first identifier 13 outputs a determination result indicating that the sound received by microphone array 20 is a cough sound. Another example is that first identifier 13 is an inference model obtained through machine learning. The inference model is obtained through training using, as training data, data obtained by adding a correct answer label to acoustic features of a cough sound and acoustic features of a sound that is not a cough sound. Upon receiving the acoustic features extracted by acoustic feature extractor 11, first identifier 13 which is the inference model as described above performs identification of the sound received by microphone array 20 and outputs a determination result indicating whether the sound is a cough sound. The determination result from identifier 13 is input to direction estimator 15.

When receiving a determination result indicating that the sound received by microphone array 20 is a cough sound, direction estimator 15 estimates the arrival direction of the sound, that is, a cough sound. Information on the arrival direction estimated by direction estimator 15 is input to image data selector 12.

The image data output by camera 30 and the estimated arrival direction of the cough sound are input to image data selector 12, as described above. Image data selector 12 selects, from the image data (first image data) received, image data (second image data) indicating an area corresponding to the arrival direction estimated by direction estimator 15. The selection of the second image data will be described later in greater detail. Image data selector 12 is an example of an image selector according to this embodiment.

Second identifier 14 performs identification of an image captured by camera 30, based on the second image data, and determines whether a coughing action is shown in the image. The identification is carried out using, for example, a statistic image model of a coughing action, which is previously prepared based on the feature data of an image showing a coughing action. The feature data is extracted from a massive amount of image data recording coughing actions. In this case, second identifier 14 extracts a feature of the second image data. When a similarity between the feature and the image model exceeds a threshold value, second identifier 14 outputs a determination result indicating that a coughing action is shown in a partial image indicated by the second image data. Another example is that second identifier 14 includes an inference model obtained through machine learning. The inference model can be obtained through training using, as training data, data obtained by adding a correct answer label to a feature of an image presenting a coughing action and a feature of an image presenting an action that is not a coughing action. Upon receiving the second image data, second identifier 14 including the inference model as described above performs identification of a partial image indicated by the second image data and outputs a determination result indicating whether a coughing action is shown in the image.

Output unit 16 performs output based on a determination result from second identifier 14. The output may be data indicating letters, an image, or sounds for presenting whether coughing has been detected to a user of cough detection device 10 ("result presentation data" in FIG. 1), for example, via a display device or a loudspeaker. Alternatively, the output may be data recorded on a determination result log ("result record data" in FIG. 1) stored in a storage device or an instruction for causing other device such as an air cleaner or a ventilator to perform a predetermined operation ("control command" in FIG. 1). Note that the receivers of the output from cough detection device 10 which are exemplified by the aforementioned display device, loudspeaker, storage device, and air cleaner may be bodies independent from cough detection device 10 and constitute one system together. Such receivers may constitute one body either by including cough detection device 10 or being included in cough detection device 10.

[2. Selections of Cough Sound Arrival Direction and Second Image Data]

The following describes the selections of a cough sound arrival direction and second image data by cough detection device 10.

In cough direction device 10, acoustic data received from microphone array 20 is used by direction estimator 15 for the estimation of the arrival direction of a sound received by microphone array 20, as described above. Second image data which is a portion indicating an area corresponding to the sound arrival direction estimated by direction estimator 15 is selected by image data selector 12 from first image data received from camera 30.

The portion indicating an area corresponding to the sound arrival direction, which is selected from the first image data, is either (i) a portion indicating a region, in which the source of the sound is shown, in an image indicated by the first image data or (ii) a portion indicating a small region that overlaps the region showing the sound source and is smaller than the entire image. A correspondence relationship between a sound arrival direction and a range of the second image data in the first image data is determined according to, for example, a positional relationship between microphone array 20 and camera 30. The correspondence relationship will be described below using an example.

Figure 2:
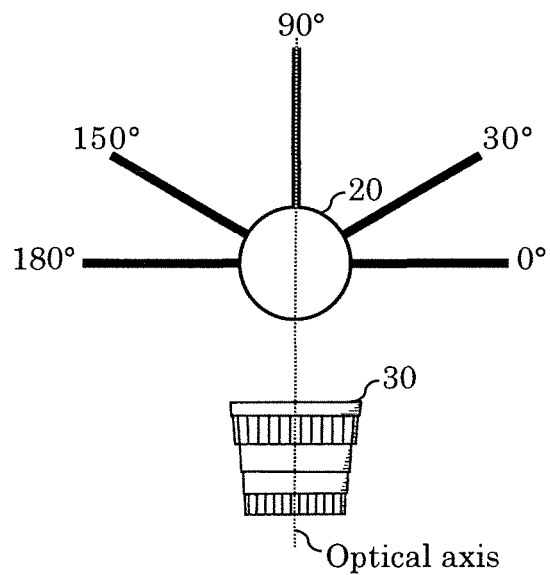
FIG. 2 is a plan view illustrating an example of a positional relationship between a microphone array and an image sensor that are used with the cough detection device.

FIG. 2 is a plan view indicating an example of the positional relationship between microphone array 20 and camera 30 in a space such as a room in which cough detection is carried out using cough detection device 10. The angles in the diagram each present a sound arrival direction estimated by direction estimator 15 using acoustic data that is input from microphone array 20 in this example. In the example, the arrival direction of a sound coming from the front of microphone array 20 is expressed by 90 degrees, the arrival direction of a sound coming from a direction that is more to the right with respect to the front is presented by an angle greater than or equal to 0 degree and less than 90 degrees, and the arrival direction of a sound coming from a direction that is more to the left with respect to the front is presented by an angle greater than 90 degrees and less than or equal to 180 degrees. Microphone array 20 and camera 30 are placed such that the front direction of microphone array 20 coincides with the optical axis (a dotted line in FIG. 2) of camera 30 in planar view. Microphone array 20 and camera 30 having such a positional relationship are installed, for example, on a wall of a room in which cough detection is carried out. Microphone 20 picks up sounds occurred in the room, and camera 30 sets, as the range of shooting, the entire area or a predetermined area in which coughing is to be detected in the room.

Figure 3:
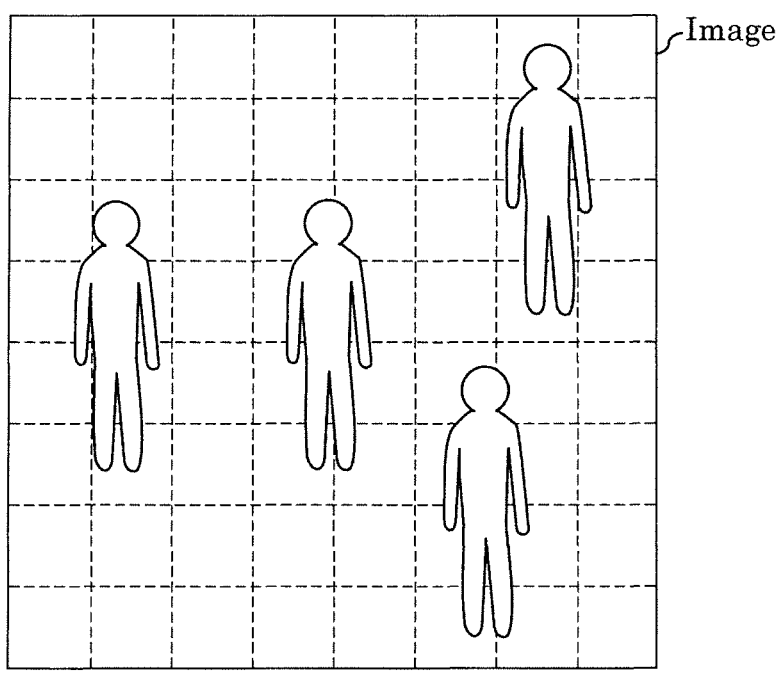
FIG. 3 is a schematic diagram illustrating a sketch of an image indicated by image data that is input from the image sensor to the cough detection device.

FIG. 3 is a schematic diagram illustrating a sketch of an image indicated by the first image data that is input from camera 30 to cough detection device 10. Note that the diagram in FIG. 3 is simplified for explaining a correspondence between the arrival direction of a sound picked up by microphone array 20 and an area in which an image is captured by camera 30, and representations that are not essential for the understanding of the concepts of the correspondence, such as perspective and distortion expressed in an image actually taken by camera 30 are omitted. The same applies to FIG. 4A through FIG. 4C that are referred to in the description below. The image illustrated in FIG. 3 shows that multiple persons are located in different places in a space in which cough detection is carried out with the use of cough detection device 10. Note also that a lattice in dotted lines illustrated in FIG. 3 presents, for convenience, an image captured by camera 30 which is sectioned into image blocks.

Figure 4A:
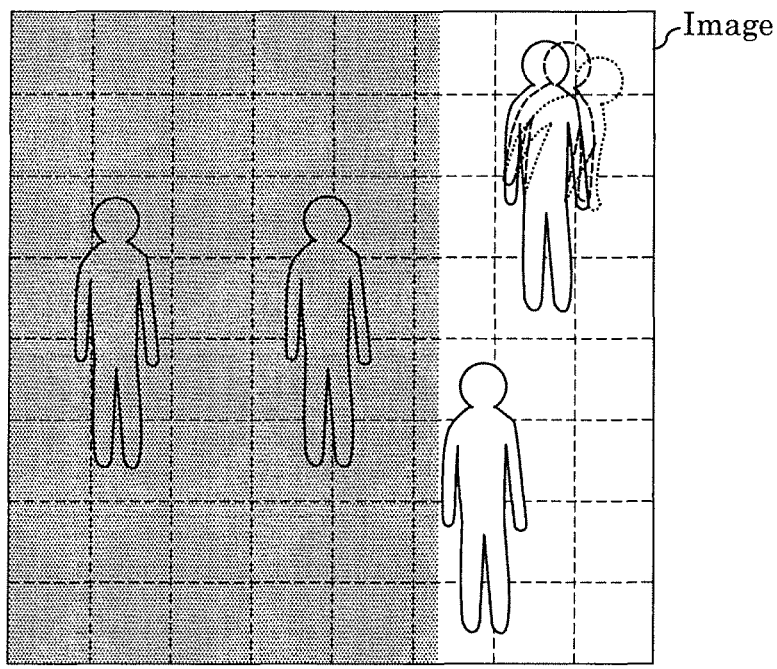
FIG. 4A is a schematic diagram for explaining a selection from image data performed by the cough detection device.

Thus, it is assumed that camera 30 that captures images of a space in which multiple persons are present and microphone array 20 are in the positional relationship as illustrated in FIG. 2. An example here assumes the following: first identifier 13 determines that a sound received by microphone array 20 is a cough sound based on acoustic features extracted by acoustic feature extractor 11 from acoustic data that is input from microphone array 20 to cough detection device 10; and the cough sound arrival direction estimated by direction estimator 15 is 30 degrees. Image data selector 12 having received an input of the arrival direction selects, from the first image data, a portion indicating an area corresponding to the arrival direction of 30 degrees. FIG. 4A is a schematic diagram for explaining the portion selected from the first image data by image data selector 12.

The image illustrated in FIG. 4A is obtained by camera 30 shooting the same space as that illustrated in FIG. 3. In this image, an unhatched region located on the right in the image corresponds to the arrival direction of 30 degrees. Image data selector 12 selects, as the second image data from the first image data, a portion presenting this region. Likewise, when the cough sound arrival direction estimated by direction estimator 15 is, for example, 90 degrees, image data selector 12 selects, as the second image data from the first image data, a portion presenting an unhatched region located near the center of the image illustrated in FIG. 4B. When the cough sound arrival direction estimated by direction estimator 15 is, for example, 150 degrees, image data selector 12 selects, as the second image data from the first image data, a portion presenting an unhatched region located on the left in the image illustrated in FIG. 4C.

Note that the selection of the second image data from the first image data by image data selector 12 may require that the identification-based determination by second identifier 14 is performed with priority given to the second image data over other portion(s) other than the second image data in the first image data.

Such identification-based determination by second identifier 14 may be performed based only on the second image data. Image data selector 12 may perform clopping or masking on an image indicated by the first image data in such a manner to leave a partial image indicated by the second image data. In the process of specifying the range of the second image data in the first image data, the range of a partial image indicated by the second image data may be specified using coordinates, for instance. In this example, first identifier 14 obtains information, such as coordinates, indicating the range of the second image data from image data selector 12, and performs identification-based determination limitedly on this range. Another example of information specifying the range of the partial image indicated by the second image data may be an identifier that indicates the range of the second image data indicating a partial image of an area corresponding to the arrival direction of a sound identified as a cough sound. The identifier is predetermined. Image data selector 12 selects an identifier indicating the range of the second image data indicating a partial image of an area corresponding to the cough sound arrival direction that has been input from direction estimator 15, and notifies second identifier 14 of the selected identifier. A concrete example assumes the case where a range indicating an unhatched region in FIG. 4A in the first image data is the range of the second image data indicating a partial image of an area corresponding to the cough sound arrival direction that is greater than or equal to 0 and less than 60 degrees, and an identifier indicating this range is predetermined as "A1". For the arrival direction of at least 60 degrees, an identifier indicating a different range is predetermined. In this case, image data selector 12, having been notified, for example, of 30 degrees as the estimated cough sound arrival direction by direction estimator 15, selects identifier "A1" and notifies second identifier 14 of the selected identifier. Second identifier 14 then performs identification-based determination using, as the second image data, a range which is indicated by identifier "A1" in the first image data.

In another example of the identification-based determination performed with priority given to the second image data over other portions other than the second image data in the first image data, the determination may be performed based also on a portion that has not been selected as the second image data in the first image data, and the importance of the second image data is still higher than that of the other portion(s) other than the second image data. The portion that has not been selected as the second image data is one of the hatched regions in FIG. 4A through FIG. 4C for visual reference. In other words, image data selector 12 selects, as the second image data from the first image data, a portion having pixels to be weighed with heavier weights. Weighing may be set such that the importance of the pixel data of the second image data in the identification-based determination is the highest in the entire first image data. The weights may be set at more than three levels for the entire first image or may be set so that the importance of pixels distant from the portion corresponding to the second image data is set lower, for example. Such weighing may be performed by image data selector 12 or image data selector 12 may perform a process up to the selection of the second image data and the weighing of the selected second image data may be performed by second identifier 14.

Figure 4B:
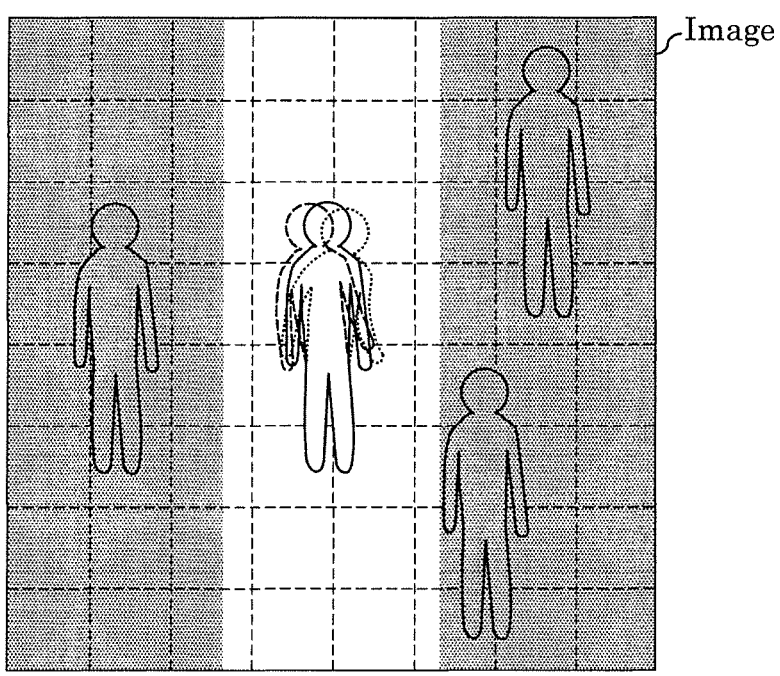
FIG. 4B is a schematic diagram for explaining a selection from image data performed by the cough detection device.
Figure 4C:
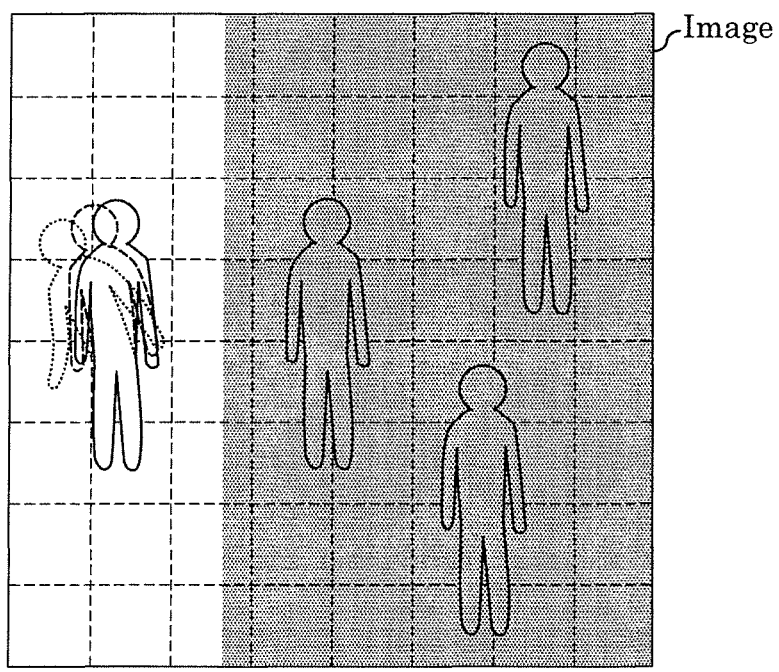
FIG. 4C is a schematic diagram for explaining a selection from image data performed by the cough detection device.

Note that in the examples illustrated in FIG. 4A through FIG. 4C, a partial image indicated by the second image data selected according to a sound arrival direction is one of the portions obtained by equally dividing an entire image indicated by the first image data, but the image is not limited to this. The size or shape of a portion indicated by the second image data selected according to a sound arrival direction, in an image indicated by the first image data, may be different. For example, the size of the portion indicated by the second image data may be different between a case where the sound arrival direction is near the center (90 degrees) of the range defined for the sound arrival direction (range greater than or equal to 0 degree and less than 180 degrees) and a case where the sound arrival direction is near an either edge (0 degree or 180 degrees) of that range. Moreover, the shape of the portion indicated by the second image data may be different according to a tendency of the figure of a person located in an area corresponding to a sound arrival direction (how the person is shown), depending on the sound arrival direction. When camera 30 is installed on a ceiling or near the ceiling, for example, the tendency in how the figure of a person is shown in a captured image may vary between a person located right below camera 30 and a person located distant from camera 30. A portion indicated by the second image data selected according to one arrival direction may overlap a portion indicated by the second image data selected according to another arrival direction.

[3. Advantageous Effects]

Cough detection device 10 having the configuration as described above performs the detection of a coughing action with a more focus on a portion presenting an area corresponding to a direction in which a sound that is highly likely to be a cough sound has occurred than other portion(s) other than that portion in an image captured by camera 30. This enables more accurate detection of a coughing action than the case of detecting a coughing action in an entire image including subjects such as persons, furniture, equipment, electrical products, etc. in a space in which cough detection is carried out.

Variation of Embodiment

A cough detection device according to one or more aspects of the present disclosure is not limited to the description of the aforementioned embodiment. Forms obtained by various modifications to foregoing embodiment that can be conceived by a person skilled in the art as well as forms realized by arbitrarily combining structural components and functions in the embodiment within the scope of the essence of the present disclosure are included in the present disclosure. The following describes examples of such a modification.

Variation 1

Figure 5:
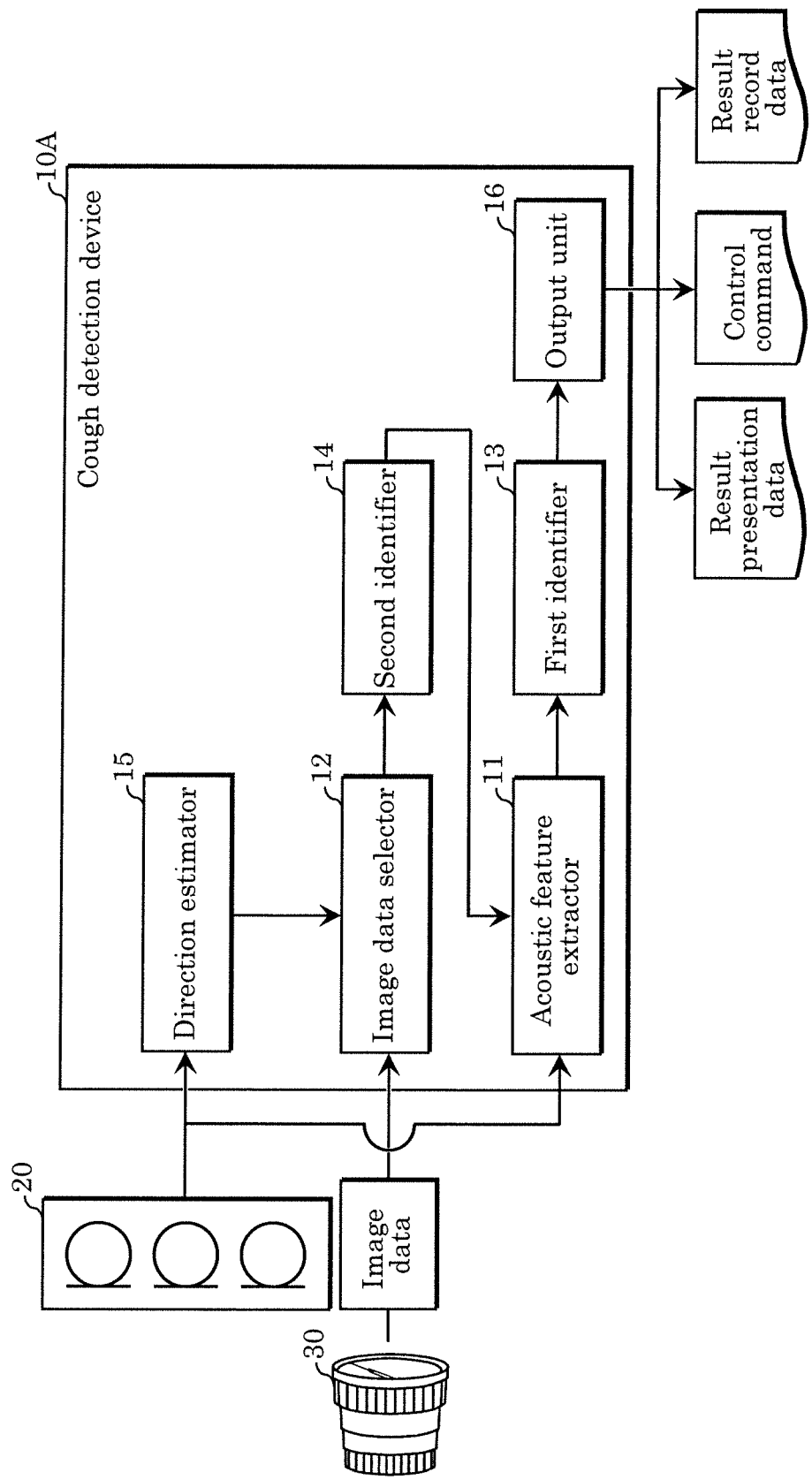
FIG. 5 is a block diagram illustrating an example of a configuration of a cough detection device according to a variation of the embodiment.

A cough detection device according to a variation of the aforementioned embodiment differs from cough detection device 10 according to the aforementioned embodiment in that image identification is performed prior to sound identification. FIG. 5 is a block diagram illustrating an example of a configuration of such cough detection device 10A. The elements in FIG. 5 which are commonly shared with cough detection device 10 are assigned with like reference signs and the following focuses mainly on the difference between this variation and the aforementioned embodiment.

A flow of data (information) between cough detection device 10A and each of the elements included therein is different from that between cough detection device 10 and each of the elements included therein. With cough detection device 10 according to the aforementioned embodiment, the extraction of acoustic features, sound identification using acoustic data output from microphone array 20, and the estimation of a sound arrival direction are performed, and then the determination of a coughing action based on image identification is performed. With cough detection device 10A, however, only the estimation of a sound arrival direction by direction estimator 15 is performed first, and sound identification is performed after the determination of a coughing action based on image identification, which is different from cough detection device 10.

Information on the sound arrival direction estimated by direction estimation 15 is input to image data selector 12, as illustrated in FIG. 5. Using the information on the estimated sound arrival direction, image data selector 12 selects, from first image data indicating an image input from camera 30, second image data which is a portion corresponding to the arrival direction. Second identifier 14 performs identification based on the second image data to determine whether a coughing action is shown in the image. Note that the determination based on the identification performed by second identifier 14 may be based only on the second image data or may be based also on other portion(s) other than the second image data but with priority given to the second image data, as is the case described in the aforementioned embodiment. The result of the determination performed by second identifier is input to acoustic feature extractor 11.

When receiving a determination result indicating that a coughing action is shown in the image, acoustic feature extractor 11 extracts acoustic features from acoustic data. Note that the acoustic features are extracted from acoustic data temporally corresponding to the image determined as showing a coughing action by second identifier 14. Then, first identifier 13 performs identification of a sound received by microphone array 20, based on the acoustic features extracted by acoustic feature extractor 11, and determines whether the sound is a cough sound.

Output unit 16 performs output based on the determination result from first identifier 13. The output is, for example, result presentation data, result record data, or a control command, as is the case described in the aforementioned embodiment.

Cough detection device 10A having the configuration as described above also performs the detection of a coughing action with a more focus on a portion presenting an area corresponding to a direction in which a sound that is highly likely to be a cough sound has occurred than other portion(s) other than that portion in an image captured by camera 30. This enables more accurate detection of a coughing action than the case of detecting a coughing action in an entire image including various subjects in a space in which cough detection is carried out.

Variation 2

Figure 6:
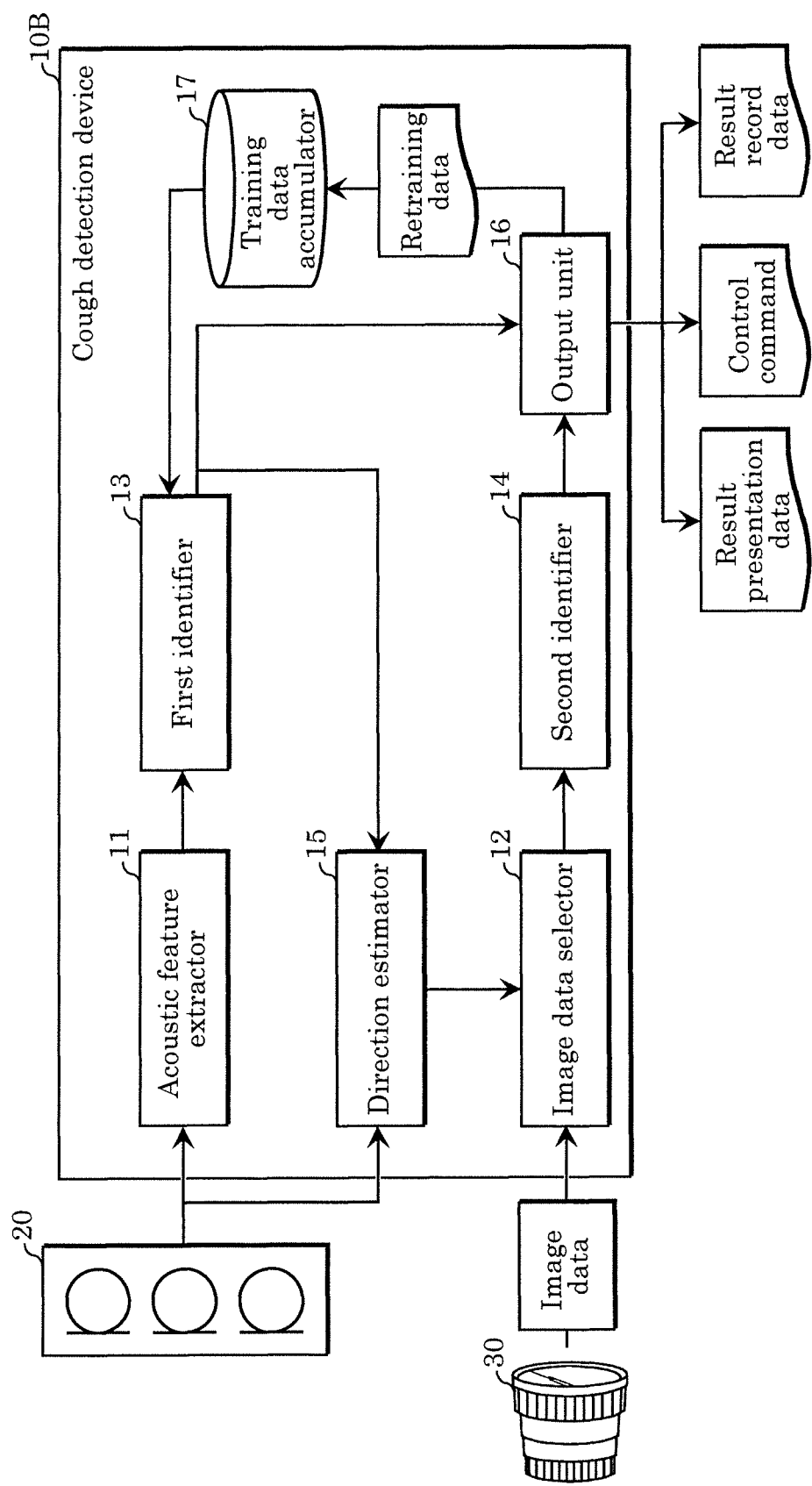
FIG. 6 is a block diagram illustrating an example of a configuration of a cough detection device according to another variation of the embodiment.

The aforementioned embodiment has described that each of first identifier 13 and second identifier 14 may be an inference model obtained through machine learning. The cough detection device according to this variation may generate data for retraining these inference models and even perform retraining using the generated data. FIG. 6 is a block diagram illustrating an example of a configuration of such cough detection device 10B. The elements in FIG. 6 which are commonly shared with cough detection device 10 are assigned with like reference signs, and the following focuses mainly on a difference between this variation and the aforementioned embodiment.

Cough detection device 10B includes, in addition to the configuration of cough detection device 10, training data accumulator 17. Training data accumulator 17 is a place where retraining data to be used for retraining of first identifier 13 is stored. Training data accumulator 17 is provided, for example, in a storage device included in an information processing device that realizes cough detection device 10B or in a storage device communicably connected to the information processing device.

Retraining data is one of data that is output from cough detection device 10B according to this variation. Output unit 16 obtains a determination result from first identifier 13 and a determination result from second identifier 14, and outputs retraining data generated based on the obtained determination results. Retraining data stored in training data accumulator 17 is used for future retraining of identifier 13.

When a determination result from first identifier 13 is different from a determination result from second identifier 14 regarding the occurrence of coughs, for example, output unit 16 may generate retraining data and output the generated data. Specifically, having obtained a determination result indicating that a sound is a cough sound from first identifier 13 and a determination result indicating that a coughing action is not shown in an image from second identifier 14, output unit 16 may combine acoustic feature data with a correction answer label indicating that the sound indicated by the acoustic feature data is a cough sound and output the combined data as retraining data.

Alternatively, output unit 16 may further obtain, from each of first identifier 13 and second identifier 14, likelihood of the determination performed by each of first identifier 13 and second identifier 14. When likelihood of the determination performed by second identifier 14 is higher than likelihood of the determination performed by first identifier 13, output unit 16 may generate retraining data as described above and output the generated data. In other words, when the likelihood of the determination, by second identifier 14, that an action shown in an image is not a coughing action exceeds the likelihood of the determination, by first identifier 13, that a sound is a cough sound, retraining data is prepared for first identifier 13 and accuracy of the identification performed by first identifier 13 is thus enhanced.

Note that a technique according to this variation is also applicable to Variation 1. In the case of applying the technique to Variation 1, having obtained a determination result, from second identifier 14, which indicates that a coughing action is shown in an image and a determination result, from first identifier 13, which indicates that a sound is not a cough sound, output unit 16 may combine image data of the image with a correct answer label indicating that an action is not a coughing action and output the combined data as retraining data. Moreover, when the likelihood of the determination, by first identifier 13, that a sound is not a cough sound exceeds the likelihood of the determination, by second identifier 14, that a coughing action is shown in an image, retraining data is prepared for second identifier 14 and accuracy of the identification performed by second identifier 14 is thus enhanced.

In this variation, in the case of using the cough detection device having the configuration illustrated in FIG. 6 with the aim to generate retraining data, the estimation of a sound arrival direction by direction estimator 15 and image identification by second identifier 14 may be performed even when first identifier 13 determines that a sound is not a cough sound. When a determination result from first identifier 13 is different from a determination result from second identifier 14 regarding the occurrence of coughs, while a combination of the determination results is not limited to the above-mentioned combination, output unit 16 may generate retraining data and output the generated data. The same applies to the case of applying the technique according to this variation to Variation 1. The extraction of acoustic features from acoustic data by acoustic feature extractor 11 and the determination based on sound identification by first identifier 13 may be performed even when second identifier 14 determines that a coughing action is not shown in an image.

With cough detection device 10B having the configuration as described above, it is possible to obtain an effect of enhancing accuracy in cough detection even after the start of the use of the device, in addition to the effects produced by cough detection device 10 and cough detection device 10A.

Variation 3

Figure 7:
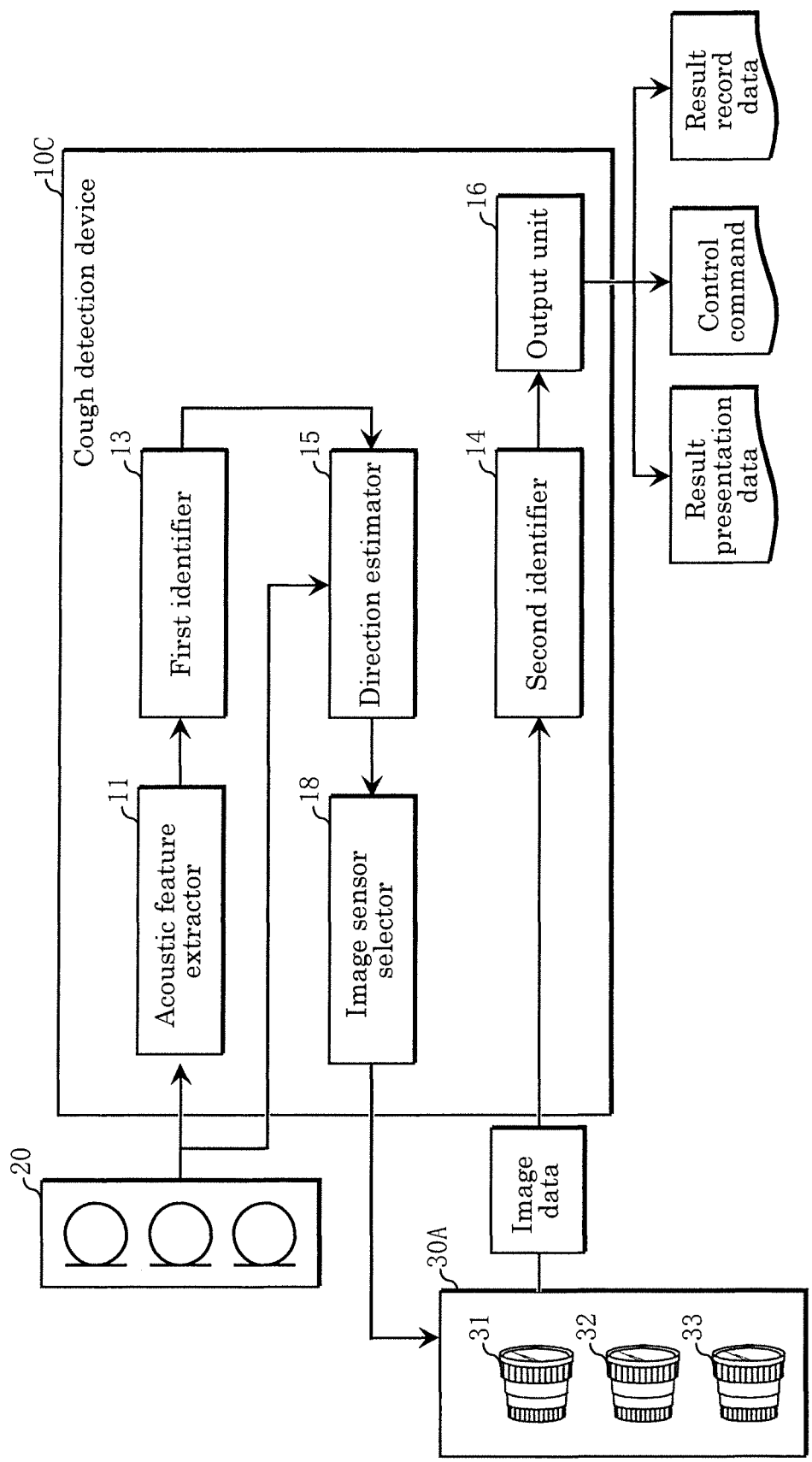
FIG. 7 is a block diagram illustrating an example of a configuration of a cough detection device according to yet another variation of the embodiment.

In each of the aforementioned embodiment and variations thereof, image data that is input to image data selector 12 indicates an image captured by an image sensor included in one camera 30. However, image data indicating an image a portion of which is captured by each of the image sensors included in cameras (hereinafter referred to as "camera group") may be input as first image data to a cough detection device, as is the case of this variation. FIG. 7 is a block diagram illustrating an example of a configuration of cough detection device 10C connected to camera group 30A including a plurality of cameras. The elements that are commonly shared with cough detection device 10 are assigned with like reference signs, and the following mainly focuses on a difference between this variation and the aforementioned embodiment.

Cough detection device 10C includes image sensor selector 18 instead of image data selector 12 in the configuration of cough detection device 10.

Camera group 30A includes cameras 31, 32, and 33. An image sensor included in each of cameras 31, 32, and 33 outputs image data indicating a captured image as first image data. The images captured by respective cameras 31, 32, and 33 are obtained by shooting at least partially different areas of a place where a sound received by microphone 20 occurs. Assuming, for example, that the image illustrated in the schematic diagram in FIG. 3 is an image captured by camera group 30A as a whole, a region indicated by the unhatched portion in the image illustrated in the schematic diagram in FIG. 4A is presented in an image obtained by camera 31 through shooting. A region indicated by the unhatched portion in the image illustrated in the schematic diagram in FIG. 4B is presented in an image obtained by camera 32, and a region indicated by the unhatched portion in the image illustrated in the schematic diagram in FIG. 4C is presented in an image obtained by camera 33.

The cough sound arrival direction estimated by direction estimator 15 is input to image sensor selector 18. Image sensor selector 18 selects (an image sensor included in) a camera installed in a location corresponding to the arrival direction estimated by direction estimator 15. The first image data output from the selected image sensor indicates an image of an area corresponding to the estimated arrival direction and is input as second image data indicating an image to be identified to second identifier 14. Such image sensor selector 18 is an example of the image selector according to this variation.

The functions of other elements are commonly shared with cough detection device 10 according to the aforementioned embodiment. In this variation, the second identifier may perform determination based on image identification that is based only on the second image data or may perform determination with priority given to the second image data while receiving also an input of the first image data that has not been selected as the second image data, for example. The technique according to this variation may be used in combination with the technique according to each of the aforementioned embodiment and variations thereof. For example, the cough detection device may include both an image data selector and an image sensor selector. In this case, image data that is output from an image sensor selected by the image sensor selector is input to the image data selector, and the image data selector selects, from the image data, a portion presenting an area that is closer to the estimated sound arrival direction. The second identifier then determines whether a coughing action is shown in the image data with priority given to the portion selected by the image data selector over other portion(s) other than the selected portion.

Variation 4

Figure 8:
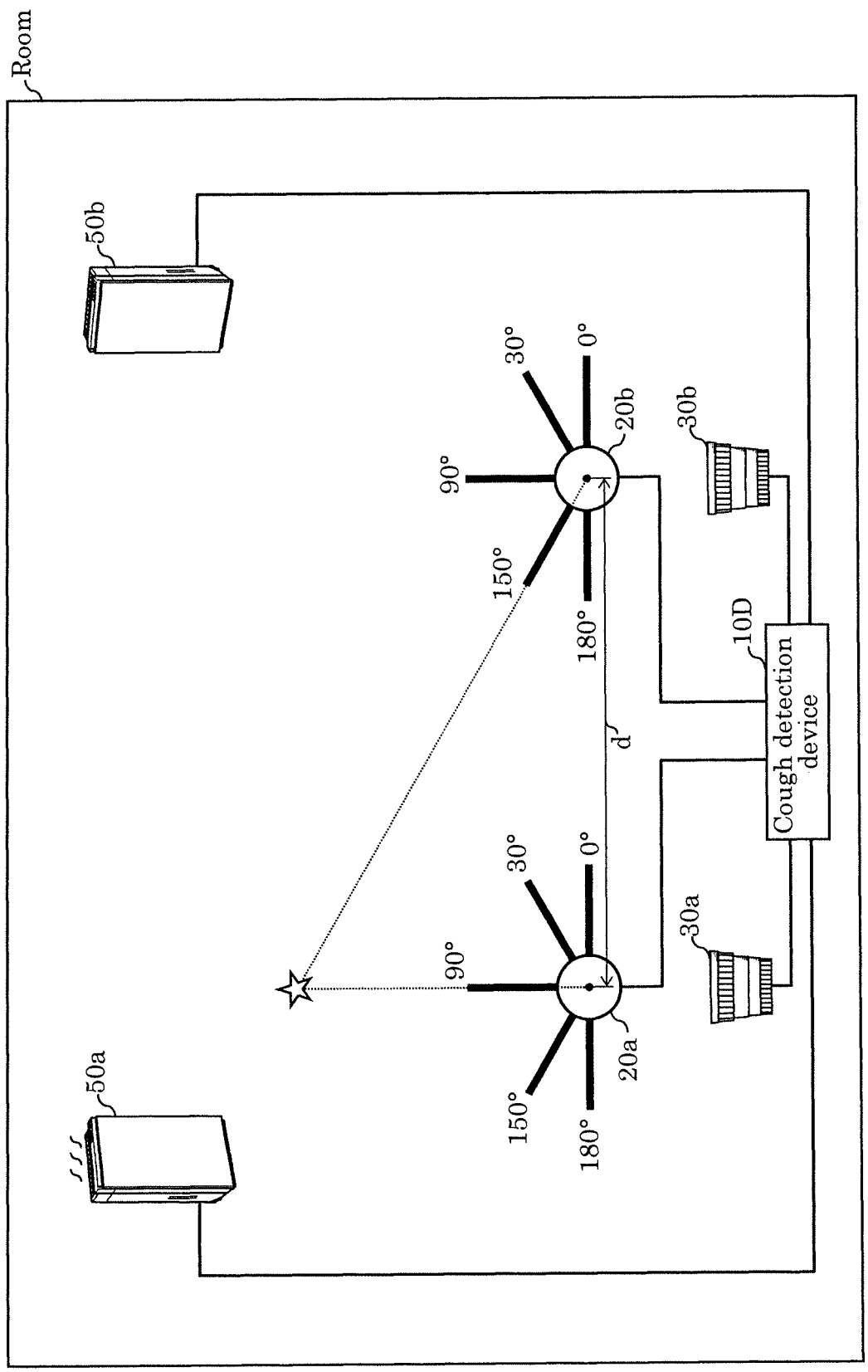
FIG. 8 is a schematic diagram for explaining a cough detection device according to yet another variation of the embodiment.

In each of the aforementioned embodiment and variations thereof, acoustic data that is input to a cough detection device has been output from one microphone array. However, with the use of a plurality of microphone arrays, as is the case of this variation, a location at which a sound occurred, not an arrival direction of the sound, may be estimated using acoustic data items that are output from the plurality of microphone arrays. FIG. 8 is a schematic diagram for explaining a cough detection device according to this variation.

Microphone arrays 20a, 20b and cameras 30a and 30b, which are installed in a room where cough detection is carried out, are connected to cough detection device 10D according to this variation, as illustrated in FIG. 8. In the room, microphone array 20a and camera 30a are in the same positional relationship as that between microphone array 20 and camera 30 illustrated in FIG. 2. Likewise, microphone array 20b and camera 30b are in the same positional relationship as that between microphone array 20 and camera 30. Moreover, a positional relationship between microphone arrays 20a and 20b is already known and is input as usable information to cough detection device 10D. Cameras 30a and 30b constitute a camera group as explained in Variation 3. Note that the number of cameras used for the technique according to this variation may be one.

The configuration of the cough detection device according to this variation may be commonly shared with any one of the cough detection devices according to the aforementioned embodiment and variations thereof. However, since a plurality of cameras are used in this variation, the following description is provided under the assumption that the configuration of cough detection device 10D is commonly shared with cough detection device 10C (see FIG. 7) according to Variation 3.

In this variation, whether each of the sounds received as inputs by microphone arrays 20a and 20b is a cough sound is determined through the processing performed by acoustic feature extractor 11 and first identifier 13 on acoustic data items that have been input from microphone arrays 20a and 20b.

Upon receiving an input of a determination result indicating that the sound received is a cough sound from first identifier 13, direction estimator 15 estimates the arrival direction of the cough sound with microphone array 20a serving as a reference, from the acoustic data received from microphone array 20a, and estimates the arrival direction of the cough sound with microphone 20b serving as a reference, from the acoustic data received from microphone array 20b. Direction estimator 15 then further estimates the occurrence location of the sound determined as a cough sound, based on the estimated arrival directions and information on the positional information between microphone arrays 20a and 20b. In the example illustrated in FIG. 8, direction estimator 15 estimates that the cough sound arrival direction with microphone array 20a serving as a reference is 90 degrees and that the cough sound arrival direction with microphone array 20b serving as a reference is 150 degrees (see dotted lines in FIG. 8). Furthermore, direction estimator 15 estimates the occurrence location of the cough sound using the information on the positional relationship between microphone arrays 20a and 20b. In the example illustrated in FIG. 8, the occurrence position of the cough sound is estimated using a triangulation method in which distance d between microphone arrays 20a and 20b is used as such information (see a star mark in FIG. 8).

In cough detection device 10D, an image sensor provided in a location corresponding to the estimated occurrence location of the cough sound is selected by image sensor selector 18. In the example illustrated in FIG. 8, an image sensor in camera 30a is selected and image data that is output by the selected image sensor is input as second image data to second identifier 14. When second identifier 14 determines that a coughing action is shown in a partial image indicated by the second image data, output unit 16 performs output according to the result of the determination. In the example illustrated in FIG. 8, cough detection device 10D is communicably connected also to air cleaners 50a and 50b.

In this case, output unit 16 may transmit a control command for the start of operation or for a switching to a mode producing antibacterial effects in a space, to air cleaner 50a located closer, between air cleaners 50a and 50b, to the occurrence location of a cough sound. With this, even when bacteria or virus that could be a causal agent is scattered in the air by coughs, it is possible to inhibit, for instance, bacteria with instantaneous effects by operating an air cleaner located closer to the occurrence location of the coughs. The examples of such devices to be controlled according to the occurrence location of a cough sound, apart from air cleaners, are air conditioners, air curtains, air circulators, ventilators, air sterilization devices using hypochlorous acid, and germicidal lamps. A device located in a predetermined location, instead of a device located closer to the occurrence location, may be a device to be controlled in accordance with the occurrence location of a cough sound, depending on the functions or arrangement of devices.

Note that even with the cough detection device according to each of the aforementioned embodiment and Variations 1 through 3, the same advantageous effects as those attained by the cough detection device according to this variation can be obtained also by controlling devices such as air conditioners in accordance with an estimated arrival direction of a cough sound. With the control on the devices in accordance with the occurrence location of a cough sound, as is the case of this variation, effects such as antibacterial effects with higher locality and effectiveness can be expected.

A combined use of various devices as described above and any one of the cough detection devices according to the present disclosure enhances effectiveness in inhibiting group infection of a disease having the risk of droplet infection at, for example, hospitals, welfare facilities for the aged, day-care centers, pre-schools, nurseries, and schools. Moreover, the combined use of the devices in general households leads to the prevention of familial infection of such a disease.

(Other Supplementary Information)

Other supplementary information for the description of the aforementioned embodiment and variations thereof is presented below.

(1) A positional relationship between a microphone array and a camera illustrated in FIG. 2 or between microphone arrays and cameras illustrated in FIG. 8 is an example and the positional relationship is not limited to such. What is required is that, irrespective of the positional relationship between a microphone array and a camera, the arrival direction of a sound, which is estimated from acoustic data output from the microphone array, is associated with a portion, of an image indicated by image data output from the camera, which includes a location at which the sound occurs. In each of the above-mentioned examples, the microphone array(s) and the camera(s) are installed on the wall of a room in which cough detection is carried out, but the installation location is not limited to this. The microphone array(s) and camera(s) may be installed, for example, on a floor near the wall of the room, at any place on the ceiling of the room, or on furniture or an electrical device in the room, or may be incorporated in a furniture or electrical device. A range set for a sound arrival direction to be estimated from acoustic data may be wider than that illustrated in the example in FIG. 2 or FIG. 8 depending on the installation location of a microphone array. In each of the examples, sound arrival directions are expressed by angles for providing a simple explanation, but the expression of the directions is not limited to this. When a microphone array is installed on the ceiling in the center of a room, for example, the sound arrival directions can be expressed using any method, such as coordinates, which enables the expression of a range including an area right below the microphone array and even to the corner of the room.

Note that the installation location of the cough detection device according to each of the aforementioned embodiment and variations thereof is not limited to a space in a room which persons targeted for cough detection frequently visit, as illustrated in FIG. 8. It is desirable that the cough detection device be communicably connected to a microphone array/microphone arrays and a camera/cameras, or also to output destinations of the output unit.

(2) In the cough detection device according to each of the aforementioned embodiment and Variations 2 to 4, when determining that a sound is a cough sound, the first identifier may input an execution command for direction estimation, instead of a determination result, to the direction estimator. Similarly, in Variation 1, when determining that a coughing action is shown in an image, the second identifier may input an execution command for acoustic feature extraction to the acoustic feature extractor.

(3) In each of the aforementioned embodiment and variations thereof, the number of the second identifier is one, but is not limited to this. A different second identifier may be used depending on a cough sound arrival direction estimated. As described above, a difference in the figure of a person who is shown (how the person is shown) in an image captured by a camera is relatively large, in some cases, depending on the positional relationship between the camera and a person who coughed. Accuracy in the identification of a coughing action can be enhanced by using the second identifier based on a model for identification specialized in a specific way in which a person is shown in an image.

(4) In the cough detection device according to each of the aforementioned embodiment and Variations 2 to 4, the output unit outputs, except retraining data, data based on a determination result output by the second identifier. The output unit in the cough detection device according to Variation 1 outputs, for instance, data based on a determination result output by the first identifier. The output from the output unit, however, is not limited to this. In each of the aforementioned embodiment and variations thereof, when a certain sound occurs, the output unit may: obtain both likelihood of determination, which is output together with a determination result by the first identifier and likelihood of determination, which is output together with a determination result by the second identifier; and output, for example, data based on the result of the determination of which the likelihood is higher. Alternatively, the output unit may output both of the determination results as result presentation data or result record data.

(5) Part or all of processing units included in an information processing device that realizes the aforementioned cough detection device may be included in system large scale integration (LSI). The system LSI is a super multi-functional LSI manufactured by integrating a plurality of components on a chip and is specifically a computer system including a microprocessor, read-only memory (ROM), and random access memory (RAM). A computer program is stored in the ROM. The system LSI achieves its function by the microprocessor operating in accordance with the computer program.

Although a system for realizing the cough detection device is introduced herein as system LSI, the system may be also referred to as IC, LSI, super LSI, or ultra LSI depending on the degree of integration. Each of the processing units to be realized as an integrated circuit is not limited to LSI and may be realized as a dedicated circuit or a general-purpose processor. A field programmable gate array (FPGA) which can be programmed after an LSI is manufactured or a reconfigurable processor which can reconfigure connection or setting of circuit cells inside an LSI may be used.

Furthermore, with the arrival of technology for circuit integration that replaces LSI owing to the progress of semiconductor technology or another technology deriving therefrom, functional blocks may be integrated using the replacing technology. The application of biotechnology, for instance, may be one possibility among others.

(6) Moreover, the elements included in the cough detection device according to each of the aforementioned embodiment and variations thereof may include, for example, a processor and a memory, and mutually communicable computers may operate in cooperation. Such elements may be realized as elements included in an information processing system providing the same functions as those included in each of the aforementioned information processing devices. In such a case, these elements are realized by part or all of the processors, which are included in each computer, executing one or more programs stored in part or all of memories included in these computers.

Figure 9:
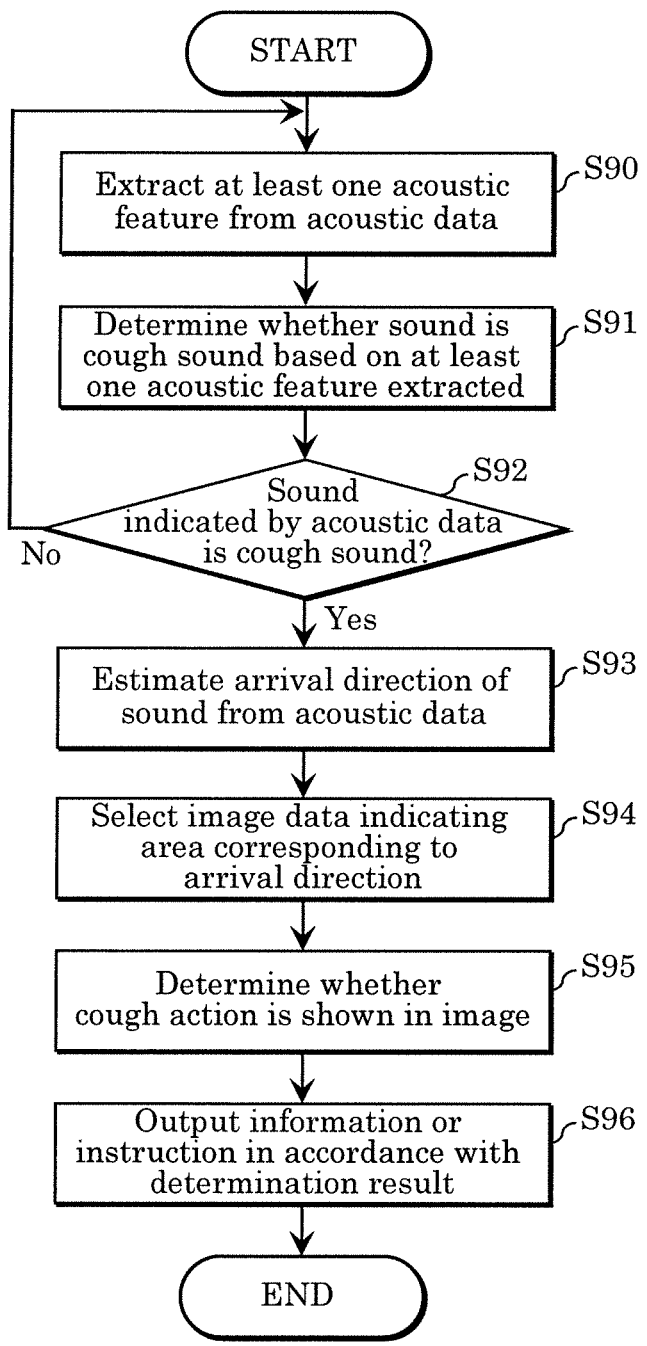
FIG. 9 is a flowchart illustrating an example of a procedure for a process of executing the cough detection device according to the embodiment.

(7) One aspect of the present disclosure is not limited to the cough detection device according to each of the aforementioned embodiment and variations thereof, and may be a cough detection method including a set of procedures for cough detection performed by characteristic elements included in the cough detection device. FIG. 9 is a flowchart illustrating a cough detection method employed by cough detection device 10 according to the embodiment. The following describes, with reference to the flowchart, an example of the cough detection method which is one aspect of the present disclosure.

In cough detection device 10, first, acoustic feature extractor 11 receives an input of acoustic data and extracts at least one acoustic feature from the acoustic data (S90).

Subsequently, first identifier 13 determines whether a sound received by microphone array 20 is a cough sound based on at least one acoustic feature extracted (S91). When the sound is not a cough sound (No in S92), the procedure of the cough detection method returns to the beginning and restarts from step S91 for the next acoustic data to be input. When the sound is a cough sound (Yes in S92), direction estimator 15 estimates the arrival direction of the sound from the same acoustic data (S93).

Then, image data selector 12 selects second image data indicating an area corresponding to the estimated arrival direction, from first image data indicating an image obtained by camera 30 capturing a scene in which the sound occurs (S94).

Subsequently, second identifier 14 determines whether a coughing action is shown in the image based on the second image data (S95).

Lastly, output unit 16 outputs data (information) or a control command (instruction) that is in accordance with the result of the determination by second identifier 14 (S96).

Note that in the case of Variation1, steps S90 through S92 are performed after steps S93 through S95. In the case of Variation 2, in step S96 performed by output unit 16, after a comparison between a determination result from first identifier 13 and a determination result from second identifier 14 or an additional comparison between the likelihoods of the determination results, retraining data is generated and output as data in accordance with the determination results. In the case of Variation 3, image sensor selector 18 selects an image sensor in step S94.

Each of the elements in each of the above-described embodiments may be configured in the form of an exclusive hardware product, or may be realized by executing a software program suitable for the element. Each of the elements may be realized by means of a program executing unit, such as a CPU and a processor, reading and executing the software program recorded on a recording medium such as a hard disk or a semiconductor memory. Here, the software program for realizing the cough detection device according to each of the embodiments is a program described below.

The program causes a computer to execute: extracting at least one acoustic feature from acoustic data that is output by a microphone array according to a sound received as an input; performing identification of the sound based on at least one acoustic feature extracted, to determine whether the sound is a cough sound; estimating an arrival direction of the sound from the acoustic data; selecting, from first image data indicating an image obtained by capturing a scene in which the sound occurs, second image data indicating an area corresponding to the arrival direction estimated; performing identification of the image based on the second image data to determine whether a coughing action is shown in the image; and determining occurrence of coughs based on at least one of a determination result indicating whether the sound is a cough sound or a determination result indicating whether a coughing action is shown in the image.

The herein disclosed subject matter is to be considered descriptive and illustrative only, and the appended Claims are of a scope intended to cover and encompass not only the particular embodiment disclosed, but also equivalent structures, methods, and/or uses.

INDUSTRIAL APPLICABILITY

A cough detection device and a cough detection method according to one or more exemplary embodiments disclosed herein are applicable to cough detection using image data and acoustic data, and can be used in combination with a technique which can be realized, for example, by air cleaners, for maintaining or improving air quality or air hygiene.

The invention claimed is:
1. A cough detection device, comprising:
an acoustic feature extractor that extracts at least one acoustic feature from acoustic data that is output by a microphone array according to a sound received as an input;
a first identifier that performs identification of the sound based on the at least one acoustic feature to determine whether the sound is a cough sound;
a direction estimator that estimates an arrival direction of the sound from the acoustic data;
an image selector that selects, from first image data indicating an image obtained by capturing a scene in which the sound occurs, second image data indicating an area corresponding to the arrival direction estimated;
a second identifier that performs identification of the image based on the second image data to determine whether a coughing action is shown in the image; and
an output unit that performs output based on at least one of a determination result from the first identifier or a determination result from the second identifier,
wherein the second identifier performs the identification of the image based also on an other portion other than the second image data in the first image data to determine whether a coughing action is shown in the image, and in the identification, priority is given to the second image data over the other portion.

2. The cough detection device according to claim 1, wherein
the direction estimator estimates the arrival direction of the sound determined as a cough sound by the first identifier.

3. The cough detection device according to claim 1, wherein
the first identifier determines whether the sound is a cough sound based on the at least one acoustic feature of the acoustic data temporally corresponding to the image determined as showing a coughing action by the second identifier.

4. The cough detection device according to claim 1, wherein
the first identifier is a first inference model obtained through machine learning, and the output unit outputs retraining data for the first inference model when the determination result from the first identifier is different from the determination result from the second identifier regarding the occurrence of coughs.

5. The cough detection device according to claim 4, wherein
the output unit further outputs the retraining data for the first inference model when likelihood of the determination by the second identifier is higher than likelihood of the determination by the first identifier.

6. The cough detection device according to claim 1, wherein
the second identifier is a second inference model obtained through machine learning, and the output unit outputs retraining data for the second inference model when the determination result from the first identifier is different from the determination result from the second identifier regarding the occurrence of coughs.

7. The cough detection device according to claim 6, wherein
the output unit further outputs the retraining data for the second inference model when likelihood of the determination by the first identifier is higher than likelihood of the determination by the second identifier.

8. The cough detection device according to claim 1, wherein
the image comprises a plurality of images obtained by a plurality of image sensors capturing at least partly different areas of the scene, and each of the plurality of image sensors outputs, as the first image data, image data of a corresponding one of the plurality of images, and
the image selector (i) selects, from among the plurality of image sensors, an image sensor provided in a location corresponding to the arrival direction estimated and (ii) causes the first image data output from the image selector to be input, as the second image data, to the second identifier.

9. The cough detection device according to claim 1, wherein
the microphone array comprises a plurality of microphone arrays,
the direction estimator estimates an occurrence location of the sound using the arrival direction estimated from a plurality of acoustic data items that are output by the plurality of microphone arrays, and
the second image data selected by the image selector indicates the area corresponding to the occurrence location estimated.

10. A cough detection method, comprising:
extracting at least one acoustic feature from acoustic data that is output by a microphone array according to a sound received as an input;
performing identification of the sound based on the at least one acoustic feature to determine whether the sound is a cough sound;
estimating an arrival direction of the sound from the acoustic data;
selecting, from first image data indicating an image obtained by capturing a scene in which the sound occurs, second image data indicating an area corresponding to the arrival direction estimated;
performing identification of the image based on the second image data to determine whether a coughing action is shown in the image; and
determining occurrence of coughs based on at least one of a determination result indicating whether the sound is a cough sound or a determination result indicating whether a coughing action is shown in the image,
wherein the identification of the image is based also on an other portion other than the second image data in the first image data to determine whether a coughing action is shown in the image, and in the identification, priority is given to the second image data over the other portion.

11. A non-transitory computer-readable recording medium for use in an information processing device including a processor and a memory, the recording medium having a computer program recorded thereon for causing the information processing device to execute the following by the processor executing the computer program stored in the memory:
extracting at least one acoustic feature from acoustic data that is output by a microphone array according to a sound received as an input;
performing identification of the sound based on the at least one acoustic feature to determine whether the sound is a cough sound;
estimating an arrival direction of the sound from the acoustic data;
selecting, from first image data indicating an image obtained by capturing a scene in which the sound occurs, second image data indicating an area corresponding to the arrival direction estimated;
performing identification of the image based on the second image data to determine whether a coughing action is shown in the image; and
determining occurrence of coughs based on at least one of a determination result indicating whether the sound is a cough sound or a determination result indicating whether a coughing action is shown in the image,
wherein the identification of the image is based also on an other portion other than the second image data in the first image data to determine whether a coughing action is shown in the image, and in the identification, priority is given to the second image data over the other portion.

* * * * *